Figure 1:
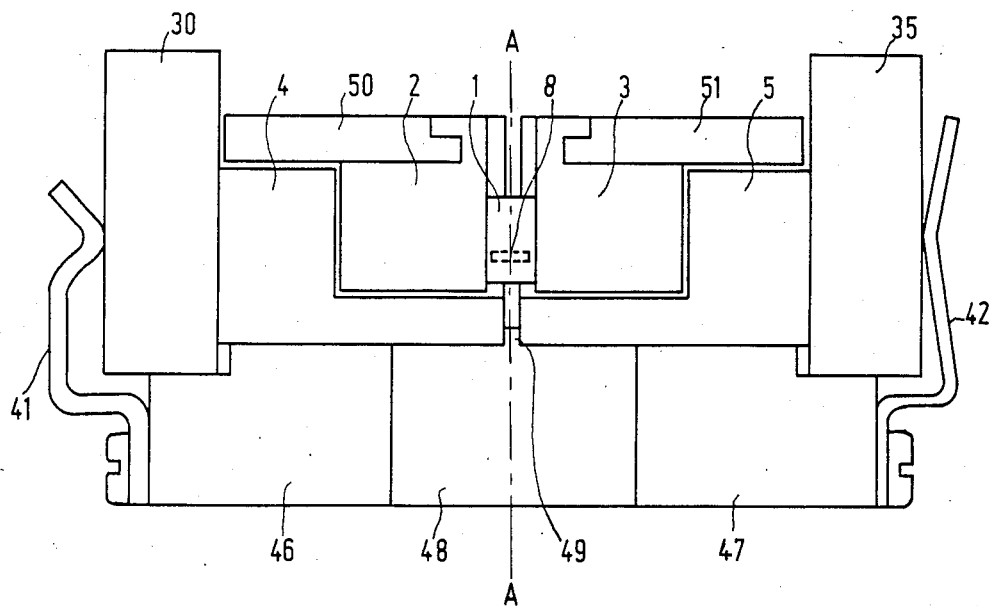

United States Patent [19]

Widmer et al.

[11] Patent Number: 4,647,200
[45] Date of Patent: Mar. 3, 1987

[54] ELECTROTHERMAL ATOMIZER

[75] Inventors: David S. Widmer; John E. Churchill, both of Cambridge, England

[73] Assignee: U.S. Philips Corporation, New York, N.Y.

[21] Appl. No.: 741,989

[22] Filed: Jun. 6, 1985

[30] Foreign Application Priority Data

Jun. 11, 1984 [GB] United Kingdom ................. 8414813

[51] Int. Cl.[4] ............................................ G01N 21/74
[52] U.S. Cl. ..................................... 356/312; 356/244
[58] Field of Search ......................... 356/244, 311, 312

[56] References Cited

U.S. PATENT DOCUMENTS 4,225,234 9/1980 Schmider et al. .................... 356/312
4,547,069 10/1985 Lersmacher et al. ............... 356/312

Primary Examiner—F. L. Evans
Assistant Examiner—Joel L. Harringa
Attorney, Agent, or Firm—Paul R. Miller

[57] ABSTRACT

An electrothermal atomizer comprises a graphite tubular member (1) which is clamped between two pairs of graphite contact members (3,5). The contact members are provided with semicircular grooves (14,22) between which the tubular member is clamped with a sufficient force to flex the wall of the tubular member to conform to the profile of the grooves. This arrangement improves the electrical contact between the tubular member (1) and the contact members (3,5) as contact over an area is provided rather than point or line contact.

11 Claims, 8 Drawing Figures

ELECTROTHERMAL ATOMIZER

The invention relates to an electrothermal atomiser for atomic spectroscopy comprising a tubular body of electrically conductive material, a first pair of contact members arranged to clamp one end of the tubular body, a second pair of contact members arranged to clamp the other end of the tubular body with, the first and second pairs of contact members acting in a direction perpendicular to the longitudinal axis of the tubular body and with means for applying an electrical potential across the tubular body via said first and second pairs of contact members.

Such an electrothermal atomiser has been manufactured and sold by Pye Unicam Limited. In this device the tubular body is provided with flanges at both ends so that it presents a rigid portion to the contact members, which are formed as copper electrodes. The flanges also provide a graphite interface between the hot (up to 3000° C.) central protion of the tubular body and the copper electrodes which are water cooled to prevent time from melting. This arrangement has certain disadvantages. The electrical contact between the copper electrodes and the flanges of the tubular body tends to be a point, or at best a line, contact since it is impossible to ensure that the surface of the flange matches that of the electrodes exactly due to manufacturing tolerances. As a result arcing between the electrodes and the flanges frequently occurs leading eventually to destruction of the electrodes and also erosion of the flanges. Further, flanged tubes are more expensive to produce than unflanged tubes. An alternative method of supplying an electrical current to the tubular body is to provide electrodes which clamp the body in the longitudinal direction. This enables tubular bodies without flanges to be used but the problem of poor electrical contact remains since the conventional form of contact is via conical surfaces which bear on the ends of the tubular body and a line contact tends to result.

It is an object of the invention to enable the provision of an electrothermal atomiser in which one or more of the disadvantages of the currently used contact mechanisms are mitigated.

The invention provides an electrothermal atomiser as set forth in the opening paragraph characterised in that the regions of the tubular body clamped by the first and second pairs of contact members are flexible and that means are provided for causing the contact members to flex the tubular body to cause the shape of the outer surface of the regions to conform to the shape of the mating part of the contact members whereby electrical contact over an area of the regions of the tubular body is produced.

An atomiser according to the invention has the advantage of a greater electrical contact area between the contact members and the tubular body since manufacturing tolerances in the components may be taken up by the flexing of the ends of the tubular body. Further the use of flanges at the ends of the tubular body is dispensed with thus reducing the manufacturing cost of the tubular body. This is particularly important when the tubular body is constructed totally of pyrolytic graphite.

Both contact members of each pair of contact members may carry a proportion of the current through the tubular body. This has the advantage of producing a more even current flow through the tubular body.

The contact members may be constructed of graphite as may the tubular body. This enables the copper electrodes which are normally water cooled to be situated further from the ends of the tubular body and the contact members may be constructed to shield the copper electrodes from the heat radiated by the tubular body and from corrosive products of the sample deposited in the tubular body.

The tubular body may be constructed totally of pyrolytic graphite and may have a circular cross section. A circular cross-section is easily produced and a predictable electrical current density around a circular body may be produced applying the electrical potentials radially over a major portion of the circumference.

Figure 2:
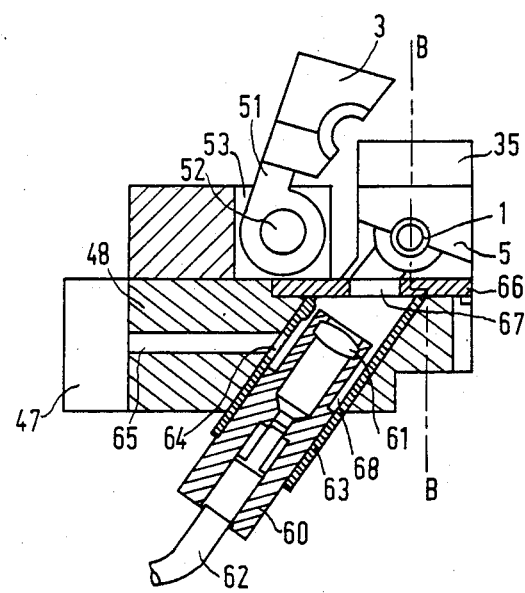
Figure 3:
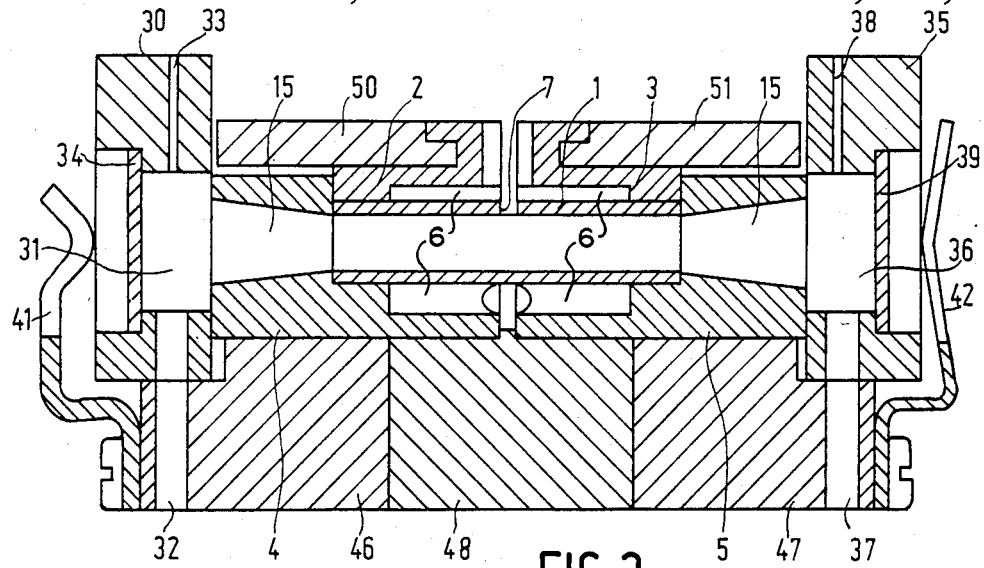
Figure 4:
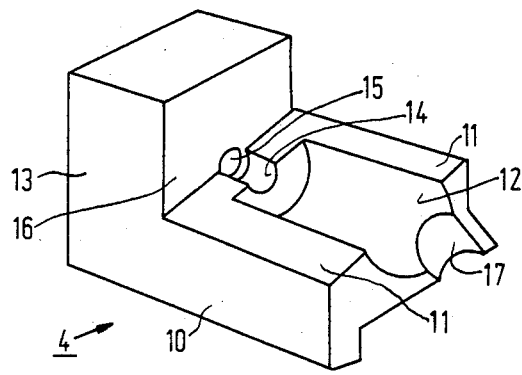
Figure 5:
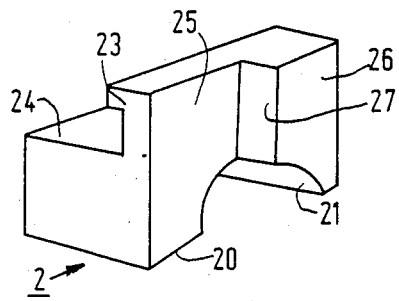
Figure 6:
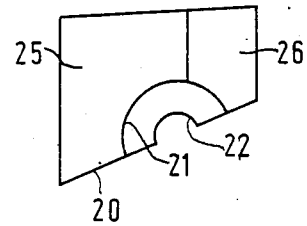
Figure 7:
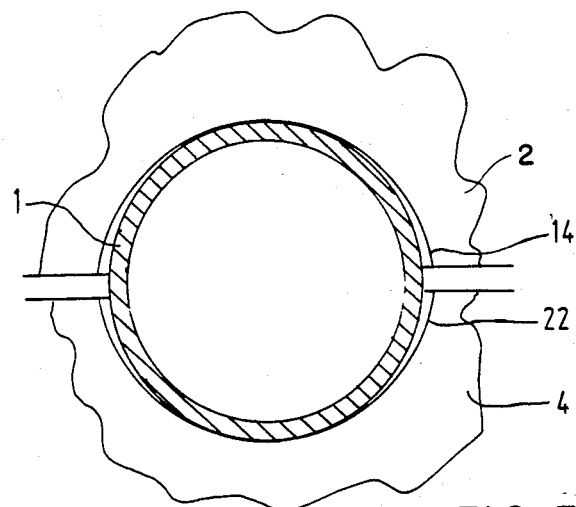
Figure 8:
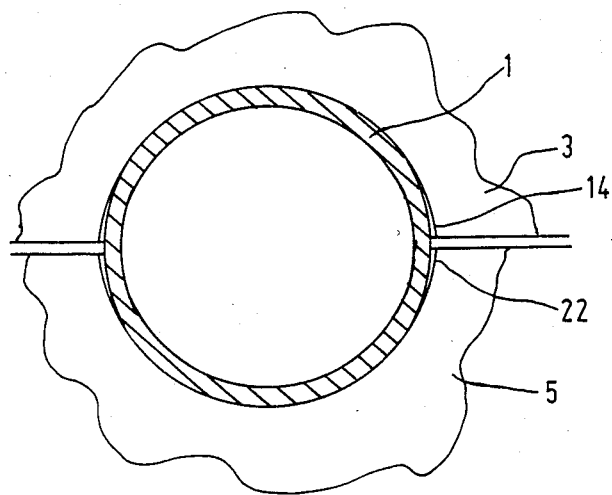

An embodiment of the invention will now be described, by way of example, with reference to the accompanying drawings, in which:

FIG. 1 shows a front elevation of an electrothermal atomiser according to the invention, FIG. 2 is a cross-sectional view on line A—A of FIG. 1 with the upper graphite contact member pivotted upwardly away from the lower graphite contact member, FIG. 3 is a cross-sectional view on line B—B of FIG. 2 with the upper and lower graphite contact members clamped together, FIG. 4 is a perspective view of the lower graphite contact member, FIG. 5 is a perspective view of the upper graphite contact member, FIG. 6 is an end elevation of the upper graphite contact member, and FIGS. 7 and 8 illustrate the interaction between the upper and lower graphite contact members and the graphite tubular member.

FIGS. 1, 2 and 3 show an electrothermal atomiser according to the invention which comprises a graphite tube 1 which, in operation, is clamped at each end between upper 2,3 and lower 4,5 graphite contact members which also provide an enclosure 6 to contain a protective gas atmosphere when the tube 1 is to be heated to high temperature. The enclosure 6 is not completely sealed as access is required to the tube 1 for inserting a sample into the tube via a dosing aperture 7 and also possibly to a slot 8 for entry of a probe through the wall of the tube 1, which entry may be achieved as described in U.K. Patent Application No. 8305745.

FIGS. 4, 5 and 6 show the form of the graphite contact members 2 and 4, the members 3 and 5 being of substantially the same form but of the opposite hand. The graphite member 4 shown in a perspective view in FIG. 4 is substantially L-shaped, the horizontal limb 10 having an inclined upper surface 11 in which is formed a semi-circular groove 12. The groove 12 extends from the free end of the limb 10 towards the other limb 13 of the member 4 but stops short of the junction of the two limbs. A semi-circular groove 14 which has a smaller radius than that of the groove 12 forms an extension of the groove 12 and extends to the other limb 13 of the member 4. The radius of the groove 14 is chosen to provide good electrical contact between the graphite member 4 and the end of the graphite tube 1, while the radius of the groove 12 is chosen to provide electrical isolation and to enable easy removal and replacement of the tube 1. The length of the groove 14 is chosen to provide the required contact surface area for efficient conduction of electrical current into the tube 1. An aperture 15 is formed in the limb 13 which aperture has a diameter substantially equal to the internal diameter of the tube 1 at the surface 16 of the limb 13 and extends through the limb 13 in the form of a truncated cone with the minimum diameter at the surface 16. A further semi-circular groove 17 extends radially into the groove 12 adjacent to the free end of the limb 10.

A perspective view of the graphite contact member 2 is shown in FIG. 5 and an end elevation is shown in FIG. 6. The member 2 comprises a rectangular block having an inclined lower face 20 in which a semi-circular groove 21 is formed, the groove 21 having the same length and diameter as the groove 12 in the member 2. A further semi-circular groove 22 having the same length and diameter as the groove 14 in the member 4 is formed between the end of the groove 12 and the hidden face of the member 2. An inverted L-shaped portion 23 extends from the upper surface 24 of the member 2. The groove 21 extends from an end which comprises two parallel faces 25, 26 separated by a step 27.

Returning to FIGS. 1 to 3, the graphite contact members 4 and 5 are mounted on copper electrodes 46 and 47 which are separated by a block 48 of electrically insulating material having an upstanding rib 49 to prevent the graphite members 4 and 5 making electrical contact with each other. A clearance gap between the rib 49 and the graphite members 46 and 47 normally exists when the tubular body 1 is inserted between the members 46 and 47 to ensure that sealing of the ends of the body 1 onto the members 46 and 47 can occur. The upper surfaces of the copper electrodes 46 and 47 are a ground finish and are maintained in the same plane to the best tolerance obtainable commercially to ensure the best possible electrical contact. The grahite contact members 4 and 5 together with the members 2 and 3 cover the copper electrodes to protect them from corrosive products from the sample, provide a seating and good electrical contact between the graphite tube 1 and the electrodes 46 and 47, and provide a means for introducing protective gas into the interior of the graphite tube 1.

A first gas entry block 30 is lightly sealed against the graphite contact member 4 and comprises a chamber 31 which is open to the aperture 15 in the graphite contact member 4 and which is provided with a gas inlet aperture 32, a bleed hole 33 and a quartz window 34. A second gas entry block 35 is lightly sealed against the graphite contact member 5 and comprises a chamber 36 which is open to the aperture 15 in the graphite contact member 5 and which is provided with a gas inlet aperture 37, a bleed hole 38 and a quartz window 39.

Thus an optical path is provided from the quartz window 34 via the chamber 31, aperture 15 in graphite contact member 4, the interior of the graphite tubular member 1, aperture 15 in graphite contact member 5, and chamber 36 to the quartz window 39. Further when the protective gas flow is stopped a volume is formed which has outlets via the bleed holes 33 and 38 and via the central dosing aperture 7 in the tubular member 1. The aperture 7 is that normally provided for inserting a sample to be atomised into the tubular member 1. If the sample is to be introduced into the tubular member 1 on a probe there may also be a further aperture (in the form of a longitudinally extending slot 8) in the tubular member 1.

The assembly of the gas entry blocks 30, 35, graphite contact members 4, 5 and graphite tubular member is located between a stop 41 mounted on the electrode 46 and a leaf spring 42 mounted on the electrode 47. The electrodes 46 and 47 and insulating block 48 are bolted together to form a rigid assembly.

As can be seen from FIG. 2 which is a cross-section on line A—A of FIG. 1 the upper graphite contact members 2, 3 are carried by copper bars 50, 51 whose other ends are pivotted on a shaft 52 mounted on end members, one of which is shown referenced 53. The upper graphite contact member 3 is shown in its raised position in FIG. 2, in which position the graphite tubular member 1 is accessible for removal or replacement. The insulating block 48 carries a temperature sensing arrangement for measuring the temperature of the tubular member 1. The temperature sensing arrangement comprises a tubular member 60 in which a lens 61 is mounted, the lens 61 focussing radiation emitted by the tubular member 1 onto the end of an optical fibre 62. The other end of the optical fibre 62 illuminates on optical pyrometer to measure the temperature of the tubular member 1. The tubular member 60 is mounted within a further tubular member 63 in the insulating block 48 the further tubular member 63 being open at both ends and having an aperture 64 in its wall with, the aperture 64 communicating with a passageway 65 in the insulating block 48. A plate 66 of ceramic material is inset into the block 48 under the graphite contact members 4 and 5 so that the material of the insulating block 48 is shielded from the high temperatures reached by the tubular member 1. The ceramic plate 66 has an aperture 67 which is aligned with the grooves 17 in the graphite contact members 4,5 to enable radiation from the tubular member 1 to pass to the lens 61. Protective gas is fed via the passageway 65 and aperture 64 to an annular chamber 68 formed between the tubular members 60 and 63 and subsequently over the lens 61 and through the aperture 67 along a channel formed by the grooves 17 in the graphite contact members 4 and 5 and round the outside of the graphite tubular member 1.

In operation a sample is deposited into the tubular member 1 through the dosing aperture 7. The temperature of the tubular member 1 is then raised to dry the sample and possibly raised still further to ash the sample depending on the composition of the sample. The drying and ashing stages may be carried out with either a flow of air or of protective gas through inlet apertures 32 and 37 and passageway 65 depending on the nature of the sample. In all cases before the temperature of the tubular body 1 is raised to the atomisation temperature a flow of protective gas is produced so that the tubular body contains and is surrounded by a protective gas. It is usual to stop the gas flow to the interior of the tubular body 1 during the atomisation phase. It has been found that if the bleed holes 33 and 38 are not present in the atomiser shown the measured chemical sensitivity is reduced. It is believed that the explanation for this phenomenon is that when the temperature of the tubular member 1 is rapidly increased the gas contained in the volume formed by the chambers 31,36, apertures 15 and the tubular body 1 expands and is forced out of the dosing aperture 7 carrying with it part of the sample. By providing an alternative escape path for the expanding gases by means of the bleed holes 33 and 38 the escape of the expanding protective gas through the dosing aperture may be substantially reduced with a corresponding reduction in the loss of sample. With the bleed holes having a diameter substantially equal to that of the dosing aperture a doubling of sensitivity has been achieved. Clearly as the diameter of the bleed holes is increased so the proportion of the gases escaping through the dosing aperture is decreased. However, there is a limit to the diameter of the bleed holes since it must be possible to fill the interior of the tubular body 1, and it is also desirable to have some scavenging action to carry away components produced during the ashing phase.

With the atomiser described access to the tubular graphite member 1 is facilitated by the horizontal split between the graphite contact members 2 and 4 and 3 and 5 since when the upper members 2 and 3 are pivoted upwardly the graphite tubular member 1 is retained between the faces 16 of the lower members 4 and 5 in the grooves 14. The tubular member 1 may then be easily removed and replaced and the orientation of the dosing aperture 7 and probe entry aperture, if provided, adjusted. The light pressure on the ends of the tubular member 1 caused by the leaf spring 42 may be mechanically relieved before removal of the tubular member if desired. This arrangement also has the advantage that the graphite contact members 4 and 5 may be easily removable since when the members 2 and 3 are pivotted upwardly no pressure is applied to the contact members 4 and 5. In practice the members 4 and 5 may be loosely fitted on the electrodes 46 and 47, for example by means of spring clips with the clamping force produced by the lowering of the upper graphite contact members 2 and 3 being sufficient to produce a good electrical connection.

FIGS. 7 and 8 illustrate how electrical contact between the ends of the tubular member 1 and the graphite contact members 2 and 4 and 3 and 5 is obtained. Each end of the tubular member 1 is located between respective upper and lower graphite contact members 2,4 and 3,5. The upper and lower graphite members are clamped together with a force which is sufficient to flex the ends of the tubular body 1 so that its external surface conforms to the internal surface of the grooves 14 and 22 in the graphite contact members. This is illustrated in FIGS. 7 and 8 where the cross-section of the tubular member 1 is shown before and after application of clamping force, respectively. It can be seen from FIG. 8 that after application of the clamping force the area of the tubular member 1 in contact with the graphite contact members has been substantially increased thus giving a better electrical connection. The tubular member 1 is normally made from graphite as this material has the necessary chemical and physical properties but the use of other materials, for example the refractory metals, is possible in some circumstances. Typical dimensions for the tubular member 1 when made from electrographite are 5 mm bore with 600 $\mu$m wall thickness. When made totally from pyrolytic graphite the wall thickness may be reduced to about 300 $\mu$m. These dimensions are purely exemplary and may be changed, for example when using probe sampling. It has been found convenient to make the external diameter of the tubular member 1 and the diameter of the grooves 14 and 22 such that a tubular member at the high end of the manufacturing tolerance has a diameter equal to the diameter of a groove 14,22 at the low end of its manufacturing tolerance. A clamping force of from 4 to 5 Kg between the graphite contact members at each end, i.e., a total clamping force of 8 to 10 Kg on the tubular member, has been found to produce a good electrical connection for tubular members having the dimensions given herein when the contact area extends over a 2 mm length of the tube.

In order to produce a desired clamping force between the graphite contact members 2 and 4 and 3 and 5 a mechanism which either pulls down the copper bars 50,51 from underneath or pushes down the copper bars from on top is required. The design of such mechanisms is well known to those skilled in the art.

We claim:

1. In an electrothermal atomizer for atomic spectroscopy comprising a tubular body of electrically conductive material and having a longitudinal axis, said tubular body having first and second open ends, a first pair of contact members clamping said first open end of said tubular body, a second pair of contact members clamping said second open end of said tubular body, said first and second pairs of contact members acting in a direction perpendicular to said longitudinal axis, and means for applying an electrical potential across said tubular body through said first and second pairs of contact members, the improvement comprising said tubular body having flexible regions clamped by said first and second contact members, and means for causing said first and second contact members to flex said tubular body to cause said flexible regions to have outer surfaces conforming to mating parts of said contact members, wherein electrical contact is provided at said flexible regions.

2. An electrothermal atomizer according to claim 1, wherein each of said first and second pairs of contact members carry a proportion of electrical current passing through said tubular body.

3. An electrothermal atomizer according to claim 1 or claim 2, wherein said contact members are provided of graphite.

4. An electrothermal atomizer according to claim 3, wherein said tubular body is provided of graphite.

5. An electrothermal atomizer according to claim 4, wherein said tubular body is provided entirely of pyrolytic graphite.

6. An electrothermal atomizer according to claim 4, wherein said tubular body has a circular cross-section.

7. An electrothermal atomizer according to claim 4, wherein said first and second contact members provide a clamping force of between 4 and 5 Kg at each end of said tubular body.

8. An electrothermal atomizer according to claim 1 or 2, wherein said tubular body is provided of graphite.

9. An electrothermal atomizer according to claim 8, wherein said tubular body is provided entirely of pyrolytic graphite.

10. An electrothermal atomizer according to claim 1 or 2, wherein said tubular body has a circular cross-section.

11. An electrothermal atomizer according to claim 1 or 2, wherein said first and second contact members provide a clamping force of between 4 and 5 Kg at each end of said tubular body.

* * * * *